(12) United States Patent
Brodie et al.

(10) Patent No.: US 6,294,540 B1
(45) Date of Patent: Sep. 25, 2001

(54) CARBOCYCLIC NUCLEOSIDE HEMISULFATE AND ITS USE IN TREATING VIRAL INFECTIONS

(75) Inventors: Alastair Couper Brodie, London; Martin Francis Jones, Kneloworth; John Frederick Seager, Ware; Christopher John Wallis, Rayston, all of (GB)

(73) Assignee: Glaxo Wellcome Inc., Research Triangle Park, NC (US)

( * ) Notice: Subject to any disclaimer, the term of this patent is extended or adjusted under 35 U.S.C. 154(b) by 0 days.

(21) Appl. No.: 09/423,982

(22) PCT Filed: May 14, 1998

(86) PCT No.: PCT/EP98/02835

§ 371 Date: Dec. 1, 1999

§ 102(e) Date: Dec. 1, 1999

(87) PCT Pub. No.: WO98/52949

PCT Pub. Date: Nov. 26, 1998

(30) Foreign Application Priority Data

May 17, 1997 (GB) .................................................. 9709945

(51) Int. Cl.$^7$ ......................... C07D 473/16; A61K 31/52; A61P 31/18
(52) U.S. Cl. .............................. 514/261; 514/220; 514/8; 424/85.2; 424/85.7; 544/277
(58) Field of Search ............................ 544/277; 514/261, 514/220, 8; 424/85.2, 85.7

(56) References Cited

FOREIGN PATENT DOCUMENTS

| 0 434 450 | 6/1991 | (EP) . |
| WO 96 06844 | 3/1996 | (WO) . |
| WO 97 49410 | 12/1997 | (WO) . |

*Primary Examiner*—Mark L. Berch
(74) *Attorney, Agent, or Firm*—Amy H. Fix

(57) ABSTRACT

The hemisulfate salt of (1S,4R)-cis-4-[2-amino-6-(cyclopropylamino)-9H-purin-9-yl]-2-cyclopentene-1-methanol or a solvate of it is used in the treatment of viral infections.

13 Claims, No Drawings

CARBOCYCLIC NUCLEOSIDE HEMISULFATE AND ITS USE IN TREATING VIRAL INFECTIONS

This application is a 35 U.S.C. §317 of PCT/EP98/02835, filed May 14, 1998.

The present invention relates to a novel salt of (1S,4R)-cis-4-[2-amino-6-(cyclopropylamino)-9H-purin-9-yl]-2-cyclopentene-1-methanol or a solvate thereof, pharmaceutical formulations containing such a compound and their use in medicine, specifically in the treatment of human immunodeficiency virus (HIV) and hepatitis B virus (HBV) infection.

(1S, 4R)-cis-4-[2-amino-6-(cyclopropylamino)-9H-purin-9-yl]-2-cyclopentene-1-methanol ('the compound') and its antiviral use, especially against HIV infections, is described in European patent Specification Number 0434450 which also refers to pharmaceutically acceptable derivatives specifically salts, esters and salts of such esters of the compound, and in particular describes hydrochloride salts of the compound. In addition PCT Patent Application No. 96/06844 describes the succinate salt of the above compound.

The compound (1S,4R)-cis-4-[2-amino-6-(cyclopropylamino)-9H-purin-9-yl]-2-cyclopentene-1-methanol is currently under clinical investigation as an anti-HIV pharmaceutical agent. There exists a need for the compound to be prepared in a form suitable for ease of isolation in large scale manufacture, and for ease of formulating into an acceptable product for administration to humans. We have found that manufacture of the free base of the compound produces an amorphous solid which traps solvents and is, therefore, unsuitable for large scale purification, or for formulation, without additional purification procedures.

Whereas the succinate salt described in PCT Patent Application No. PCT/GB95/02014 has advantages in its preparation, for example, it forms the salt easily from stoichiometric ratios of the acid and base and crystallises very easily out of solution, it is not an ideal subject for pharmaceutical formulation, specifically tableting. In particular, the succinate salt of the compound agglomerates to form a 'lumpy' mass which will not easily pour and is thus unsuitable for use in commercial tableting machines, such that an extra processing step of high energy milling is required to give a uniform particle size. An additional complication attendent upon formulation of the succinate salt of the compound is that it can exist in several crystal forms, each form having slightly different physical properties. The preparation of the succinate salt of the compound requires close attention to avoid the preparation of undesired forms, which if formed require reworking to the desired form.

We have found that the advantages of the hemisulfate salt of the compound over the disclosed hydrochloride salts and succinate salt renders the hemisulfate salt particularly suitable and advantageous to prepare on a large scale, and in particular for use in the preparation of pharmaceutical formulations. Specifically the hemisulfate salt forms a free flowing powder, which lacks any undue tendency to agglomerate, and which is easily poured and compacted, and thus ideal for use in commercial tableting machines without the need for milling. The salt is believed to exist as a single morphic and crystalline form. The salt does not readily hydrate or solvate (e.g. on storage). The salt filters and dries readily, thereby assisting ease of preparation. A further advantage is the higher aqueous solubility of the hemisulfate as compared to the succinate, which makes the hemisulfate particularly suitable for the preparation of liquid formulations.

We have also found that where the hemisulfate salt is prepared by a 'salt exchange' process, that is to say by conversion of a precursor salt of (1S,4R)-cis-4-[2-amino-6-(cyclopropylamino)-9H-purin-9-yl]-2-cyclopentene-1-methanol, particularly the glutarate or succinate salt, an enrichment in optical purity over that of the precursor salt is achievable. Thus, the need for any further preparative or purification steps to enhance the optical purity of the hemisulfate salt product may be reduced or eliminated.

According to the first aspect of the invention there is provided the hemisulfate salt of (1S,4R)-cis-4-[2-amino-6-(cyclopropylamino)-9H-purin-9-yl]-2-cyclopentene-1-methanol or a solvate thereof, including a hydrate thereof, hereinafter referred to as the compound according to the invention.

For the avoidance of doubt, as used herein, the hemisulfate salt of (1S,4R)-cis4-[2-amino-6-(cyclopropylamino)-9H-purin-9-yl]-2-cyclopentene-1-methanol means the salt formed between (1S,4R)-cis4-[2-amino-6-(cyclopropylamino)-9H-purin-9-yl]-2-cyclopentene-1-methanol and sulfuric acid in a stoichiometric ratio of 2:1.

Further aspects of the invention include:

a) The compound of the invention for use in medicine, particularly in the treatment of viral infections, specifically an HIV or an HBV infection.

b) A method for the treatment of a viral infection particularly an HIV or an HBV infection in a human which comprises administering to said human an effective amount of the compound according to the invention.

c) Use of a compound according to the invention in the manufacture of a medicament for the treatment of a viral infection particularly an HIV or an HBV infection.

The compound of the invention is particularly useful for the treatment of HIV infections.

It will be appreciated by those skilled in the art that reference herein to treatment extends to prophylaxis as well as the treatment of established infections or symptoms.

Examples of clinical conditions caused by HIV infections which may be treated in accordance with the invention include Acquired Immune Deficiency Syndrome (AIDS) or symptoms that frequently precede AIDS, or related clinical conditions such as AIDS-related complex (ARC), progressive generalised lymphadenopathy (PGL), Kaposis sarcoma, thrombocytopenic purpura, AIDS related neurological conditions, such as multiple sclerosis or tropical paraparesis and also anti-HIV antibody-positive and HIV-positive conditions including AIDS asymptomatic patients.

The compounds of the invention may be administered alone or in combination with other therapeutic agents suitable in the treatment of HIV infections, such as Nucleoside Reverse Transcriptase Inhibitors (NRTIs) for example zidovudine, zalcitabine, lamivudine, didanosine, stavudine, 5-chloro-2',3'-dideoxy-3'-fluorouridine, adefovir and (2R,5S)-5-fluoro-1-[2-(hydroxymethyl)-1,3-oxathiolan-5-yl]cytosine, lovaride, non-NRTIs for example nevirapine, delavuridine, α-APA, HBY-1293 and efavirenz HIV protease inhibitors for example saquinavir, indinavir, nelfinavir, ritonavir and VX-478, other anti-HIV agents for example soluble CD4, immune modulators for example interleukin II, erythyropoetin, tucaresol, and interferons for example α-interferon. In addition the compound of the invention may be administered in combination with other therapeutic agents suitable in the treatment of HBV infections for example lamivudine, (2R,5S)-5-fluoro-1-[2-

(hydroxymethyl)-1,3-oxathiolan-5-yl]cytosine, immune modulators, and interferons as described above. Such combinations may be administered together or sequentially providing that any duration between the administration of each therapeutic agent does not diminish their additive effect.

While it is possible for the compound of the invention to be administered as the raw chemical, it is preferable and advantageous to present the compound of the invention as a pharmaceutical formulation, and represents a further feature of the invention. The pharmaceutical formulation comprises the compound of the invention together with one or more acceptable carrier(s) therefor and optionally other therapeutic agents. The carrier(s) must be "acceptable" in the sense of being compatible with the other ingredients of the formulation and not deleterious to the recipients thereof.

The compounds according to the invention may be administered by any route appropriate to the condition to be treated, suitable routes including oral, rectal, nasal, topical (including transdermal, buccal and sublingual), vaginal and parenteral (including subcutaneous, intramuscular, intravenous, intradermal, intrathecal and epidural). It will be appreciated that the preferred route may vary with, for example, the condition of the recipient.

For each of the above-indicated utilities and indications the amount required of the individual active ingredient will depend upon a number of factors including the severity of the condition to be treated and the identity of the recipient and will ultimately be at the discretion of the attendant physician. In general, however, for each of these utilities and indications, a suitable, effective dose will be in the range of 1 to 120 mg per kilogram body weight of recipient per day, preferably in the range of 3 to 90 mg per kilogram body weight per day and most preferably in the range of 5 to 60 mg per kilogram body weight per day such as 5 to 20 mg per kilogram body weight per day. The dose may if desired be presented as two, three, four or more sub-doses administered at appropriate intervals throughout the day.

The formulations include those suitable for oral, rectal, nasal, topical (including buccal and sublingual), vaginal or parenteral (including subcutaneous, intramuscular, intravenous, intradermal, intrathecal and epidural) administration. The formulations may conveniently be presented in unit dosage form and may be prepared by any of the methods well known in the art of pharmacy. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, or paste or may be contained within liposomes.

A tablet may be made by compression or moulding, optionally with one or more accessory ingredients. Compressed tablets may be prepared by compressing in a suitable machine the active ingredient in a free-flowing form such as a powder or granules, optionally mixed with a binder (e.g. povidone, gelatin, hydroxypropylmethyl cellulose), lubricant, inert diluent, disintegrant (e.g. sodium starch glycollate, cross-linked povidone, cross-linked sodium carboxymethyl cellulose), surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein using, for example, hydroxypropylmethyl-cellulose in varying proportions to provide the desired release profile.

A capsule may be made by filling a loose or compressed powder or an appropriate filling machine, optionally with one or more additives. Examples of suitable additives include binders such as povidone, gelatin, lubricants, inert diluents, disintegrants as for tablets. Capsules may also be formulated to contain pellets or discrete sub-units to provide slow or controlled release of the outline ingredient. This can be achieved by extruding and spheronising a wet mixture of the drug plus an extrusion acid (e.g. microcrystalline cellulose) plus a diluent such as lactose. The spheroids thus produced can be coated with a semi-permeable membrane (e.g. ethyl cellulose, Eudragit WE30D) to produce sustained release properties.

For infections of the eye or other external tissues, e.g., mouth and skin, the formulations are preferably applied as a topical ointment or cream containing the active ingredient in an amount of, for example, 0.075 to 20% w/w, preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base or as in a water in oil base.

If desired, the aqueous phase of the cream base may include, for example, at least 40–45% w/w of a polyhydric alcohol, i.e. an alcohol having two or more hydroxyl groups such as propylene glycol, butane-1,3-diol, mannitol, sorbitol, glycerol and polyethylene glycol and mixtures thereof. The topical formulations may desirably include a compound which enhances absorption or penetration of the active ingredient through the skin or other affected areas. Examples of such dermal penetration enhancers include dimethylsulfoxide and related analogues.

The oily phase of the emulsions of this invention may be constituted from known ingredients in a known manner. While this phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabiliser. It is also preferred to include both an oil and a fat. Together, the emulsifier(s) with or without stabiliser(s) make up the so-called emulsifying wax, and the wax together with the oil and/or fat make up the so-called emulsifying ointment base which forms the oily dispersed phase of the cream formulations.

Emulgents and emulsion stabilisers suitable for use in the formulation of the present invention include Tween 60, Span 80, cetostearyl alcohol, myristyl alcohol, glyceryl monostearate and sodium lauryl sulphate.

According to a first process (A), the compound of the invention may be prepared by admixture of sulfuric acid and (1S,4R)-cis4-[2-amino-6(cyclopropylamino)-9H-purin-9-yl]-2-cyclopentene-1-methanol in a stoichiometric ratio of approximately 1:2, preferably in solution, more preferably in an aqueous organic solvent, preferably at elevated temperature, more preferably at the reflux temperature of the chosen solvent system. Upon cooling, crystals of the compound of the invention form. Preferably crystallisation is effected by 'seeding' the solution with a small quantity of the compound of the invention. Optional washing and recrystallisation may be used to improve the purity of the product.

According to an alternative process (B), the compound of the invention may be formed by admixture of (1S,4R)-cis4-[2-amino-6-(cyclopropylamino)-9H-purin-9-yl]-2-cyclopentene-1-methanol monosulfate (1:1 salt) and (1S,4R)-cis-4-[2-amino-6-(cyclopropylamino)-9H-purin-9-yl]-2-cyclopentene-1-methanol in a substantially 1:1 molar ratio in solution.

A particularly advantageous process (C) for preparing the compound of the invention comprises conversion of a salt of (1S,4R)-cis-4-[2-amino-6-(cyclopropylamino)-9H-purin-9-yl]-2-cyclopentene-1-methanol to the compound of the invention. Suitable salts for conversion include dicarboxylic acid salts such as the succinate, glutarate, hemisuberate (i.e. salt formed from 2:1, base: suberic acid), adipate, fumarate, hemisebacate (i.e. salt formed from 2:1, base: sebacic acid), and pimelate salts. Mixtures of dicarboxylic acid salts may be employed. Use of the succinate and glutarate salts is preferred. Preparation of the succinate salt is described in PCT Application No. PCT/GB95/02014. Other salts of (1S,4R)-cis-4-[2-amino-6-(cyclopropylamino)-9H-purin-9-yl]-2-cyclopentene-1-methanol useful for conversion to the hemisulfate include the benzoate and salicylate salts and mixtures thereof. Such salts represent a further feature of the invention.

In one preferred aspect of the present invention, the conversion may be effected by admixture of sulfuric acid and a salt of (1S,4R)-cis-4-[2-amino-6(cyclopropylamino)-9H-purin-9-yl]-2-cyclopentene-1-methanol other than the hemisulfate in the appropriate stoichiometric ratio. For the avoidance of doubt, the appropriate stoichiometric ratio (i.e. salt of (1S,4R)-cis-4-[2-amino-6(cyclopropylamino)-9H-purin-9-yl]-2-cyclopentene-1-methanol:sulfuric acid) will be 2:1 if the salt is a 1:1 salt (i.e. ratio of (1S,4R)-cis-4-[2-amino-6(cyclopropylamino)-9H-purin-9-yl]-2-cyclopentene-1-methanol to acid is 1:1) and 1:1 if the salt is a 2:1 salt (i.e. ratio of (1S,4R)-cis-4-[2-amino-6 (cyclopropylamino)-9H-purin-9-yl]-2-cyclopentene-1-methanol to acid is 2:1). The admixing is preferably carried out in solution, more preferably in an aqueous organic solvent, preferably at elevated temperature, more preferably at the reflux temperature of the chosen solvent system. The hemisulfate crystals are formed upon cooling of the reaction mixture, optionally with seeding, as previously described. This process of salt interconversion provides advantages in terms of the purity of the compound of the invention thereby obtained.

A particularly advantageous feature of the process of conversion of the abovementioned salts to the hemisulfate is that the conversion results in an enhancement of optical purity, i.e. there is a lesser amount of the unwanted (1R, 4S) isomer in the compound of the invention thus produced than there was in the starting salt.

Suitable solvents for use in the processes of the invention include alcohols such as, for example, ethanol or propan-2-ol. Such solvents may be used alone or in admixture, optionally in the presence of a further organic solvent, such as acetone, or in the presence of water, thereby forming an aqueous organic solvent mixture.

The compound (1S,4R)-cis4-[2-amino-6-(cyclopropylamino)-9H-purin-9-yl]-2-cyclopentene-1-methanol can be synthesised in accordance with European Patent Specification Number 0434450 or alternatively PCT Application No. PCT/GB/9500225 which are incorporated herein by reference.

The succinate salt of the compound (1S,4R)-cis4-[2-amino-6-(cyclopropylamino)-9H-purin-9-yl]-2-cyclopentene-1-methanol can be synthesised in accordance with PCT Patent Application No. PCT/GB95/02014, which is incorporated herein by reference.

The invention is further described in the following examples which are illustrative thereof and not limiting thereto.

As used in the following examples, IMS means industrial methylated spirits (denatured ethanol) and IPA means propan-2-ol.

INTERMEDIATE 1

Preparation of (1S,4R)-cis-4-[2-amino-6-(cyclopropylamino)-9H-purin-9-yl]-2-cyclopentene-1-methanol (1S,4R)-cis-4-[2-amino-6-chloro-9H-purin-9-yl]-2-cyclopentene-1-methanol hydrochloride salt (EP0434450 (80 g)) was heated under reflux in industrial methylated spirits (800 ml) with cyclopropylamine (110 ml) for about 5 h. The mixture was cooled to 70 to 75° C. and an aqueous solution of sodium hydroxide (10 M, 55 ml, 2 molar equivalents) was added dropwise. The resultant suspension was cooled to 20 to 25° C. and filtered, the collected solids being washed with IMS (2×60 ml). The combined filtrates and washings were treated with charcoal (8 g) and the filter-aid Harborlite J2 (4 g) then heated to 40 to 50° C. After about 0.5 h, the mixture was cooled to 15 to 20° C. and the solids were removed by filtration, washed with IMS (2×160 ml and 1×80 ml) and the combined filtrates and washings were concentrated by distillation under reduced pressure to a residual volume of about 240 ml. IMS (560 ml) was added and the mixture was concentrated under reduced pressure to a residual volume of about 240 ml. The dilution and reconcentration was repeated and the resultant concentrate was diluted with IMS (240 ml) and heated to obtain a complete solution which was divided into four equal portions.

One portion was concentrated by distillation under reduced pressure to a residual volume of about 60 ml. Acetone (140 ml) was added and the mixture re-concentrated to about 60 ml. This dilution and re-concentration was repeated twice to give a fluid volume of about 80 ml. The resultant suspension was cooled to 0 to 5° C. and the product was filtered, washed with cold (0 to 5° C.) acetone (2×40 ml) and dried in vacuo to give the title compound as an orange solid (16.8 g, 90%);$^1$H-NMR (D$_2$O) δ:7.71(s, 1, purine CH), 6.22(m, 1, =CH), 5.93(m, 1, =CH), 5.37(m, 1, NCH), 3.61(m, 2, OCH$_2$), 3.04(br m, 1, CH of cyclopropyl), 2.82(br m, 1,CH), 2.80–2.70(m, 1, CH), 1.58–1.50(m, 1, CH), 0.90–0.60(m, 4, 2×CH$_2$ of cyclopropyl).

EXAMPLE A

Preparation of (1S,4R)-cis-4-[2-amino-6-(cyclopropylamino)-9H-purin-9-yl]-2-cyclopentene-1-methanol hemisulfate salt.

A stirred mixture of water (25 ml) and IPA (100 ml) was heated to 45 to 55° C. and (1S,4R)-cis-4-[2-amino-6-(cyclopropylamino)-9H-purin-9-yl]-2-cyclopentene-1-methanol succinate salt (WO96/06844 (50 g)) was added, and washed in with IPA (12.5 ml). The mixture was heated under reflux for about 0.5 h to give a clear solution and then cooled to 65 to 75° C. and a solution of concentrated sulfuric acid (6.07 g) in water (12.5 ml) was added. A mixture of IPA (37.5 ml) and water (12.5 ml) was added and the solution was cooled to 45 to 55° C., whereupon a seed of authentic (1S,4R)-cis-4-[2-amino-6-(cyclopropylamino)-9H-purin-9-yl]-2-cyclopentene-1-methanol hemisulfate salt was added. After stirring in this temperature range for about 1 h to allow crystallisation to become established, further IPA (300 ml) was added, maintaining the temperature of the mixture in the range 45 to 55° C. The suspension was cooled to 0 to 5° C. over about 2 h, and the product was filtered, washed with IPA (2×75 ml), and dried in vacuo at 40 to 45° C. to give the title compound as a fawn coloured powder (34.3 g, 90%); m.p. 224–225° C. (decomp.);$^1$H-NMR (DMSO-d6) δ:10.76 (br m, 1, purine NH), 8.53(vbr m, 1, NH), 7.80(s, 1, purine CH), 6.67(br m, 1, NH$_2$), 6.13(m, 1, =CH), 5.87(m, 1, =CH), 5.40(m, 1, NCH), 3.45(d, J=5.8 Hz, 2, OCH$_2$), 2.96(br m, 1, CH of cyclopropyl), 2.87(m, 1, CH), 2.67–2.57 (m, 1, CH), 1.65–1.55(m, 1, CH), 0.84–0.64(m, 4, 2×CH$_2$ of cyclopropyl).

EXAMPLE B

Preparation of (1S,4R)-cis-4-[2-amino-6-(cyclopropylamino)-9H-purin-9-yl]-2-cyclopentene-1-methanol hemisulfate salt.

A stirred suspension of (1S,4R-cis-4-[2-amino-6-(cyclopropylamino)-9H-purin-9-yl]-2-cyclopentene-1-methanol succinate salt (WO96/06844 (1000 g)) in industrial methylated spirit (IMS) (7000 ml) was heated under reflux for about 0.5 h to obtain a clear solution. The solution was cooled to about 70° C. and a solution of concentrated sulfuric acid (121 g) in IMS (1000 ml) was added. After seeding with authentic (1S,4R-cis-4-[2-amino-6-(cyclopropylamino)-9H-purin-9-yl]-2-cyclopentene-1-methanol hemisulfate salt, the mixture was stirred at about 70° C. to allow the product to crystallise. After about 0.5 h, the mixture was cooled to 20 to 30° C. over about 2 h. The mixture was filtered, the cake was washed with IMS (2×2000 ml) and dried in vacuo at 40 to 45° C. to give the title compound as a fawn coloured powder (764 g, 92%), spectra identical to those of the product of Example A.

EXAMPLE C

Preparation of (1S,4R)-cis-4-[2-amino-6-(cyclopropylamino)-9H-purin-9-yl]-2-cyclopentene-1-methanol hemisulfate salt A suspension of (1S,4R)-cis-4-[2-amino-6-(cyclopropylamino)-9H-purin-9-yl]-2-cyclopentene-1-methanol succinate salt (10 g) in industrial methylated spirit (IMS) (30 ml) and water (5 ml) was heated under reflux for about 0.5 h to give a clear solution. The solution was cooled to 55 to 65° C. and a solution of concentrated sulfuric acid (1.21 g) in water (2.5 ml) was added, followed by a mixture of IMS (7.5 ml) and water (2.5 ml). The solution was further cooled to 45 to 55° C. and acetone (80 ml) was added over about 0.25 h to the mixture within this temperature range. The resultant suspension was cooled to 0 to 5° C. over about 1 h. The product was filtered, washed with acetone (2×10 ml) and dried in vacuo at 40 to 45° C. to give the title compound as a fawn coloured powder (6.28 g, 82%) which was spectroscopically identical to the product of Example A.

EXAMPLE D

Preparation of (1S,4R)-cis-4-[2-amino-6-(cyclopropylamino)-9H-purin-9-yl]-2-cyclopentene-1-methanol hemlsulfate salt (1S,4R)-cis-4-[2-amino-6-(cyclopropylamino)-9H-purin-9-yl]-2-cyclopentene-1-methanol (Intermediate 1) (5.98 g) was suspended in IMS (40 ml) and the suspension was heated under reflux for about 0.5 h. The mixture was cooled to 70 to 75° C. and a mixture of a solution of concentrated sulfuric acid in IMS (10M, 1.03 ml, 0.5 molar equivalent) and IMS (10 ml) was added dropwise. The acid was washed in with further IMS (10 ml) and the resultant suspension was cooled to 0 to 5° C. The product was isolated by filtration, washed with IMS (2×12 ml) and dried in vacuo at 40 to 45° C. to yield the tile compound as a pale yellow solid (6.15 g, 88%), spectra identical to those of the product of Example A.

EXAMPLE E

Preparation of (1S,4R)-cis-4-[2-amino-6-cyclopropylamino)-9H-purin-9-yl]-2-cyclopentene-1-methanol hemisulfate salt A further portion of the IMS solution of Intermediate 1 was heated to 75 to 80° C. to ensure complete solution. This was cooled to 70 to 75° C. and a solution of concentrated sulfuric acid (3.90 g) in IMS (30 ml) was added dropwise, to give an orange coloured suspension. The mixture was cooled to 0 to 5° C. over about 2 h and the product was filtered, washed with IMS (2×40 ml) and dried in vacuo at 40 to 45° C. to give the title compound as a yellow/orange solid (17.7 g, 76%), spectra identical to those of the product of Example A.

Of this product, 5.0 g was suspended in a mixture of isopropanol (IPA) (40 ml) and water (10 ml) and heated under reflux for about 0.5 h and then allowed to cool to 55 to 60° C., whereupon seeds of authentic (1S,4R)-cis-4-[2-amino-6-(cyclopropylamino)-9H-purin-9-yl]-2-cyclopentene-1-methanol hemisulfate salt were added. The suspension was cooled further to 0 to 5° C. and the temperature was maintained for about 1 h. The solid was filtered, washed with IPA (2×5 ml) and dried in vacuo at 40 to 45° C. to yield the title compound as a buff coloured powder (4.4 g, 88%), spectra identical to those of the product of Example A.

EXAMPLE F (1S,4R)-cis-4-[2-amino-6-(cyclopropylamino)-9H-purin-9-yl]-2-cyclopentene-1-methanol benzoate salt (1S,4R)-cis-4-[2-amino-6-chloro-9H-purin-9-yl]-2-cyclopentene-1-methanol hydrochloride salt EP0434450 (70 g) was heated under reflux in IMS (700 ml) with cyclopropylamine (94.5 ml) for about 4 h. The solution was cooled to 45 to 50° C. and treated with filter-aid Harborlite J2 (3.5 g) and charcoal (7 g). After about 0.5 h, the mixture was cooled to 20 to 25° C. and filtered. The solids were washed with IMS (2×140 ml) and the combined filtrates and washings were concentrated by distillation under reduced pressure to a volume of about 210 ml. After dilution with IMS, (490 ml) the solution was re-concentrated to about 210 ml. The dilution and reconcentration was repeated once and the final concentrate was divided into seven equal portions.

One portion was diluted with IMS (80 ml) and warmed until a complete solution was obtained. Benzoic acid (4.85 g) was added as a single portion and the mixture was heated at 70 to 75° C. to give a complete solution, which was then allowed to cool slowly. At 40 to 45° C. the mixture was seeded with authentic (1S,4R)-cis-4-[2-amino-6-(cyclopropylamino)-9H-purin-9-yl]-2-cyclopentene-1-methanol benzoate salt and the mixture was further cooled to 0 to 5° C. The solid was filtered, washed with IMS (2×20 ml) and dried in vacuo at 40 to 45° C. to give the title compound as a white solid (8.7 g, 64%), mpt: 156–157° C.; $^1$H-NMR (DMSO-d$_6$) δ:7.95(m, 2, benzoate CH), 7.63(m, 1, benzoate CH), 7.61(s, 1, purine CH), 7.50(m, 2, benzoate CH), 7.28(br m, 1, NH), 6.11(m, 1, =CH), 5.86(m, 1, =CH), 5.81 (br m, 1, OH), 5.39(m, 1, NCH), 3.45(d, J=6.0 Hz, 2, OCH$_2$), 3.04(br m, 1, CH of cyclopropyl), 2.87(br m, 1, CH), 2.65–2.55(m, 1, CH), 1.63–1.53(m, 1, CH), 0.70–0.54(m, 4, 2×CH$_2$ of cyclopropyl).

EXAMPLE G

Preparation of (1S,4R)-cis-4-[2-amino-6-(cyclopropylamino)-9H-purin-9-yl]-2-cyclopentene-1-methanol hemisulfate salt A suspension of (1S,4R)-cis-4-[2-amino-6-(cyclopropylamino)-9H-purin-9-yl]-2-cyclopentene-1-methanol benzoate salt (5 g) in IPA (25 ml) was warmed to 60 to 65° C. A solution of concentrated sulfuric acid (0.64 g) in water (1.25 ml) was added and the resultant cloudy suspension was warmed to 70 to 75° C. The mixture was cooled to 20 to 25° C. and filtered. The solid was washed with IPA (2×10 ml) and dried in vacuo at 40 to 45° C. to give the title compound as a white solid (3.57 g, 87%), spectra identical to those of the product of Example A.

EXAMPLE H

Preparation of (1S,4R)-cis-4-[2-amino-6-(cyclopropylamino)-9H-purin-9-yl]-2-cyclopentene-1-methanol glutarate salt.

(1S,4R)-cis-4-[2-amino-6-chloro-9H-purin-9-yl]-2-cyclopentene-1-methanol hydrochloride salt (EP0434450) (25 g) was heated under reflux in IMS (250 ml) with cyclopropylamine (30 ml) for about 4 h. The solution was cooled to 45 to 50° C., diluted with IMS (75 ml) and treated with charcoal (1 g) and filter-aid Harborlite J2 (0.5 g). After about 1 h, the mixture was cooled to 20 to 25° C. and filtered. The solids were washed with IMS (50 ml) and the combined filtrates and washings were diluted with IMS (150 ml) and then concentrated by distillation under reduced pressure to about 75 ml. The mixture was diluted with IMS (90 ml) and re-concentrated to about 75 ml. The process of dilution and re-concentration was repeated twice more. The final concentrate was diluted with IMS (75 ml) and heated to 70 to 75° C. to give a solution. To this was added a solution of glutaric acid (13 g) in IMS (75 ml) which had been pre-heated to 70 to 75° C. The mixture was further diluted with IMS (25 ml) and cooled to about 25° C. over about 2 hours. The mixture was further cooled to 0 to 5° C., stirred for about 2 hours and filtered. The product was washed with IMS (2×50 ml) and dried in vacuo at about 45° C. to furnish the title compound as a light brown solid (27.1 g, 78%); mp. 184–188° C.; $^1$H-NMR (DMSO-d$_6$) δ:7.60(s, 1, purine CH), 7.27(br m, 1, NH), 6.10(m, 1, =CH), 5.86(m, 1, =CH), 5.82(br m, 1, OH), 5.39(m, 1, NCH), 3.44(d, J=5.9 Hz, 2, OCH$_2$), 3.04(br m, 1, CH of cyclopropyl), 2.87(br m, 1, CH), 2.65–2.55(m, 1, CH), 2.24(t, J=7.2 Hz, 4, glutarate 2×CH$_2$), 1.70(m, J=7.2 Hz, 2, glutarate CH$_2$), 1.62–1.54(m, 1, CH), 0.68–0.54(m, 4, 2×CH$_2$ of cyclopropyl).

EXAMPLE I

Preparation of (1S,4R)-cis-4-[2-amino-6-(cyclopropylamino)-9H-purin-9-yl]-2-cyclopentene-1-methanol hemisulfate salt.

A suspension of (1S,4R)-cis-4-[2-amino-6-(cyclopropylamino)-9H-purin-9-yl]-2-cyclopentene-1-methanol glutarate salt (20 g) in a mixture of IPA (80 ml) and water (20 ml) was heated to reflux to give a solution. The solution was cooled to about 75° C. and a solution of concentrated sulfuric acid (2.4 g) in water (5 ml) was added. The resultant solution was diluted with a mixture of IPA (16 ml) and water (4 ml) and then with IPA (20 ml). The solution was cooled to 50 to 55° C., seeded with authentic (1S,4R)-cis-4-[2-amino-6-(cyclopropylamino)-9H-purin-9-yl]-2-cyclopentene-1-methanol hemisulfate salt and stirred for about 30 minutes. To the resultant suspension was added IPA (160 ml) over about 15 minutes then the suspension was cooled to about 25° C. over about 2 hours and then to about 0–5° C. After stirring for a further 2 hours the product was filtered, washed with IPA (2×40 ml) and dried in vacuo at about 45° C. to give the title compound as a light brown solid (14.98 g, 93%), spectra identical to those of the product of Example A.

EXAMPLE J

Preparation of (1S,4R)-cis-4-[2-amino-6-(cyclopropylamino)-9H-purin-9-yl]-2-cyclopentene-1-methanol hemisulfate salt from the succinate salt in the presence of its enantiomer A mixture of (1S,4R)-cis-4-[2-amino-6-(cyclopropylamino)-9H-purin-9-yl]-2-cyclopentene-1-methanol, succinate salt and its enantiomer (134 g) having an enantiomeric ratio of 97.5:2.5 as shown by chiral HPLC (eluant (1.0 v/v acetonitrile in aqueous 0.05M potassium phosphate buffer, pH 6.5; column ChromTech Chiral-AGP, 100×4.0 mm; flow 1.0 ml/min; detection at 220 nm) was suspended in isopropanol (IPA) (302 ml) and water (67 ml) and heated to reflux to give a clear solution. The solution was cooled to 75 to 80° C. and a solution of concentrated sulfuric acid (16.26 g) in water (33.5 ml) was added, and the solution was clarified by a hot filtration, following through the filter with a mixture of IPA and water (3:1, 134 ml). The filtrates and washings were cooled to 45 to 50° C. and seeded with authentic(1S,4R)-cis-4-[2-amino-6-(cyclopropylamino)-9H-purin-9-yl]-2-yclopentene-1-methanol, hemisulfate salt. Further IPA (804 ml) was added in this temperature range and the resultant suspension was cooled to 0 to 5° C. The suspension was filtered and the product was washed with IPA (2×200 ml) and dried in vacuo at 40 to 45° C. to give the title compound as a white crystalline solid (75 g, 68%).

Analysis of the product by chiral HPLC (conditions as above) showed the ratio of enantiomers to be 99.2:0.8.

A range of similar experiments was carried out on 8 g scale using different ratios of enantiomers of the input succinate salt with the same experimental protocol. The results are summarised below in tabular form:

| RATIO OF ENANTIOMERS OF INPUT SUCCINATE SALT | RATIO OF ENANTIOMERS OF PRODUCT HEMISULFATE SALT |
| --- | --- |
| 99.5:0.5 | 99.9:0.1 |
| 99.0:1.0 | 99.7:0.3 |
| 98.0:2.0 | 99.5:0.5 |
| 96.0:4.0 | 99.0:1.0 |

EXAMPLE K

Preparation of (1S,4R)-cis-4-[2-amino-6-(cyclopropylamino)-9H-purin-9-yl]-2-cyclopentene-1-methanol hemisulfate salt from the glutarate salt in the presence of its enantiomer A mixture of (1S,4R)-cis-4-[2-amino-6-(cyclopropylamino)-9H-purin-9-yl]-2-cyclopentene-1- methanol, glutarate salt and its enantiomer (100 g) having an enantiomeric ratio of 98.6:1.4 as shown by chiral HPLC (conditions as above in Example J) was suspended in isopropanol (IPA) (400 ml) and water (100 ml) and heated to reflux to give a clear solution. The solution was cooled to 70 to 75° C. and a solution of concentrated sulfuric acid (12.01 g) in water (25 ml) was added, followed by a mixture of IPA and water (4:1, 100 ml) and then by IPA (100 ml). The solution was cooled to 50 to 55° C. and seeded with authentic (1S,4R)-cis-4-[2-amino-6-(cyclopropylamino)-9H-purin-9-yl]-2-cyclopentene-1-methanol, hemisulfate salt. Further IPA (800 ml) was added in this temperature range and the resultant suspension was cooled to 0 to 5° C. The suspension was filtered and the product was washed with IPA (2×200 ml) and dried in vacuo at 40 to 45° C. to give the title compound as a white crystalline solid (72 g, 90%).

Analysis of the product by chiral HPLC (conditions as above in Example J) showed the ratio of enantiomers to be 99.6:0.4.

EXAMPLE L

Preparation of (1S,4R)-cis-4-[2-amino-6-(cyclopropylamino)-9H-purin-9-yl]-2-cyclopentene-1-methanol salicylate salt (1S,4R)-cis-4-[2-amino-6-(cyclopropylamino)-9H-purin-9-yl]-2-cyclopentene-1-methanol (Intermediate 1) (1.0 g) and salicylic acid (0.482 g) were heated in IMS (about 25 ml) until a clear solution was formed. This was allowed to cool to about 20° C. and the resultant suspension was filtered and the solid product dried in vacuo at about 40° C. to give the title compound as a white solid, (1.163 g, 78%); m.pt: 195–198° C.; $^1$H-NMR (dmso-$d_6$) δ: 7.78(d of d, J=7.7 Hz, J=1.7 Hz, 1H, aromatic CH); 7.66(s, 1H, purine CH); 7.66(br m, 1H, NH); 7.43–7.48(m, 1H, aromatic CH); 6.85–6.92(m, 2H, 2×aromatic CH); 6.11(m, 1H, =CH); 6.11(br m, 1H, OH); 5.87(m, 1H, =CH); 5.40(m, 1H, NCH); 3.45(m, 2H, OCH$_2$); 3.03(br m, 1H, CH of cyclopropyl); 2.87(m, 1H, CH); 2.55–2.65(m, 1H, CH); 1.63–1.55(m, 1H, CH); 0.73–0.58(m, 4, 2×CH$_2$ of cyclopropyl).

The so-formed salicylate salt may be converted to the desired hemisulfate salt by a method analogous to that described at Example G for conversion of the benzoate salt to the hemisulfate salt.

EXAMPLE M

Preparation of (1S,4R)-cis-4-[2-amino-6-(cyclopropylamino)-9H-purin-9-yl]-2-cyclopentene-1-methanol monosulfate salt A stirred suspension of (1S,4R)-cis-4-[2-amino-6-(cyclopropylamino)-9H-purin-9-yl]-2-cyclopentene-1-methanol (10.00 g) in industrial methylated spirits (IMS) (40 ml) was heated to 60° C. to obtain a clear solution. A solution of concentrated sulfuric acid (6.99 g) in IMS (15 ml) was added dropwise, and the mixture was heated under reflux for about 0.25 h to once more obtain a clear solution. This mixture was cooled to 20 to 30° C. over about an hour, with crystallisation occurring during the cooling. This suspension was further cooled to 0 to 5° C. over about 0.25 h, and stirred for about 1 h within this temperature range. The product was filtered, washed with IMS (2×15 ml), and dried in vacuo at 40 to 45° C. to give the title compound as a fine white powder (9.07 g, 67.5%);$^1$H-NMR (DMSO-d6) δ:0.78 (2H, m), 0.93 (2H, m), 1.10 (3H, t, J 7.1 Hz) (ethanol), 1.63 (1H, dt, J 13.8, 5.5 Hz), 2.64 (1H, dt, J 13.8, 8.8 Hz), 2.8–3.0 (3H broad m), 3.46 (2H, m), 3.74 (2H, q, J 7.1 Hz) (ethanol), 5.42 (1H, m), 5.88 (1H, m), 6.17 (1 H, m), 5.4–7.8 (broad, exchangeable), 8.0 (1H, s).

EXAMPLE N

Preparation of (1S,4R)-cis-4-[2-amino-6-(cyclopropylamino)-9H-purin9-yl]-2-cyclopentene-1-methanol hemisulfate salt A stirred suspension of (1S,4R)-cis-4-[2-amino-6-(cyclopropylamino)-9H-purin-9-yl]-2-cyclopentene-1-methanol monosulfate salt (5.00 g), and (1S,4R)-cis4-[2-amino-6-(cyclopropylamino)-9H-purin-9-yl]-2-cyclopentene-1-methanol (3.725 g) in isopropanol (IPA) (30 ml) and water (10 ml) was heated under reflux for about 0.25 h to obtain a clear solution. The solution was cooled to about 50 to 55° C., and IPA (40 ml) was added over about 0.25 h maintaining the temperature at 50 to 55° C. Crystallisation occurred during the addition. The mixture was cooled to 20 to 30° C. over about an hour, then further cooled to 0 to 5° C. over about 0.25 h, and stirred for about 1 h within this temperature range. The product was filtered, washed with IPA (2×10 ml), and dried in vacuo at 40 to 45° C. to give the title compound as a fine white powder (5.17 g, 59.1%), spectra identical to those of the product of Example A.

EXAMPLE 1

Tablet Formulations

The following formulations A, B and C are prepared by wet granulation of the ingredients with a solution of povidone, followed by addition of magnesium stearate and compression.

Formulation A

|     |                          | mg/tablet | mg/tablet |
| --- | ------------------------ | --------- | --------- |
| (a) | Active ingredient        | 250       | 250       |
| (b) | Lactose B.P.             | 210       | 26        |
| (c) | Povidone B.P.            | 15        | 9         |
| (d) | Sodium Starch Glycollate | 20        | 12        |
| (e) | Magnesium Stearate       | 5         | 3         |
|     |                          | 500       | 300       |

Formulation B

|     |                          | mg/tablet | mg/tablet |
| --- | ------------------------ | --------- | --------- |
| (a) | Active ingredient        | 250       | 250       |
| (b) | Lactose                  | 150       | —         |
| (c) | Avicel PH 101            | 60        | 26        |
| (d) | Povidone B.P.            | 15        | 9         |
| (e) | Sodium Starch Glycollate | 20        | 12        |
| (f) | Magnesium Stearate       | 5         | 3         |
|     |                          | 500       | 300       |

Formulation C1 (Controlled Release Formulation)

The formulation is prepared by wet granulation of the ingredients (below) with a solution of povidone followed by the addition of magnesium stearate and compression.

|     |     |     | mg/tablet |
| --- | --- | --- | --- |
| (a) | Active Ingredient | | 500 |
| (b) | Hydroxypropylmethylcellulose (Methocel K4M Premium) | | 112 |
| (c) | Lactose B.P. | | 53 |
| (d) | Povidone B.P.C. | | 28 |
| (e) | Magnesium Stearate | | 7 |
| | | | 700 |

Capsules are prepared by dispersing the active ingredient in the lecithin and arachis oil and filling the dispersion into soft, elastic gelatin capsules.

Formulation C (Controlled Release Capsule)

The following controlled release capsule formulation is prepared by extruding ingredients a, b, and c using an extruder, followed by spheronisation of the extrudate and drying. The dried pellets are then coated with release-controlling membrane (d) and filled into a two-piece, hard gelatin capsule.

|     |     | mg/capsule |
| --- | --- | --- |
| (a) | Active Ingredient | 250 |
| (b) | Microcrystalline Cellulose | 125 |
| (c) | Lactose BP | 125 |
| (d) | Ethyl Cellulose | 13 |
| | | 513 |

Formulation D (Film Coated Tablet)

The following film coated tablet is prepared using a direct compression process. The hemlsufate salt of (1S,4R)-cis-4-[2-amino-6-(cyclopropylamino)-9H-purin-9-yl]-2-cyclopentene-1-methanol is sifted and blended with microcrystalline cellulose and sodium starch glycolate. Magnesium stearate and colloidal silicon dioxide are then sifted and blended with the other ingredients. The blend is compressed into tablets which are then coated using standard film coating technology.

|     | Tablet Core | mg/tablet |
| --- | --- | --- |
| (a) | hemisulfate salt | 351.0 |
| (b) | Microcrystalline Cellulose | 414.6 |
| (c) | Sodium Starch Glycolate | 24.0 |
| (d) | Magnesium Stearate | 8.0 |
| (e) | Colloidal Silicon Dioxide | 2.4 |
| | Total Core Tablet Weight | 800.0 |

Tablet Coat

|     |     |     |
| --- | --- | --- |
| (f) | Opadry ™ Yellow | 24.0 (g) |
| (g) | Puritied Water USP | q.s. |
| | Total Tablet Weight | 824.0 |

The amount of colloidal silicon dioxide present in the tablet core may be varied to e.g. 0.8 mg.

EXAMPLE 2

Injectable Formulation

| | |
| --- | --- |
| Active ingredient | 0.200 g |
| Sterile, pyrogen free phosphate buffer (pH 7.0) to | 10 ml |

The active ingredient is dissolved in most of the phosphate buffer (35–40° C.), then made up to volume and filtered through a sterile micropore filter into a sterile 10 ml amber glass vial (type 1) and sealed with sterile closures and overseals.

EXAMPLE E

Intramuscular Injection

| | | |
| --- | --- | --- |
| Active Ingredient | | 0.20 g |
| Benzyl Alcohol | | 0.10 g |
| Glycofurol 75 | | 1.45 g |
| Water for Injection | q.s. to | 3.00 ml |

The active ingredient is dissolved in the glycofurol. The benzyl alcohol is then added and dissolved, and water added to 3 ml. The mixture is then filtered through a sterile micropore filter and sealed in sterile 3 ml glass vials (type 1).

EXAMPLE 4

Syrup Suspension

| | |
| --- | --- |
| Active ingredient | 0.2500 g |
| Sorbitol Solution | 1.5000 g |
| Glycerol | 2.0000 g |
| Dispersible Cellulose | 0.0750 g |
| Sodium Benzoate | 0.0050 g |
| Flavour, Peach 17.42.3169 | 0.0125 ml |
| Purified Water q.s. to | 5.0000 ml |

The sodium benzoate is dissolved in a portion of the purified water and the sorbitol solution added. The active ingredient is added and dispersed. In the glycerol is dispersed the thickener (dispersible cellulose). The two dispersions are mixed and made up to the required volume with the purified water.

EXAMPLE 5

Suppository

| | mg/suppository |
| --- | --- |
| Active Ingredient | 250 |
| Hard Fat, BP (Witepsol H15 - Dynamit Nobel) | 770 |
| | 1020 |

The active ingredient is used as a powder wherein at least 90% of the particles are of 63 μm diameter or less.

One-fifth of the Witepsol H15 is melted in a steam-jacketed pan at 45° C. maximum. The active ingredient is sifted through a 200 μm sieve and added to the molten base with mixing, using a silverson fitted with a cutting head, until a smooth dispersion is achieved. Maintaining the mixture at 45° C., the remaining Witepsol H15 is added to the suspension and stirred to ensure a homogenous mix. The entire suspension is passed through a 250 μm stainless steel screen and, with continuous stirring, is allowed to cool to 45° C. At a temperature of 38° C. to 40° C. 2.02 g of the mixture is filled into suitable plastic moulds. The suppositories are allowed to cool to room temperature.

EXAMPLE 6
Pessaries

|  | mg/pessary |
| --- | --- |
| Active ingredient | 250 |
| Anhydrous Dextrose | 380 |
| Potato Starch | 363 |
| Magnesium Stearate | 7 |
|  | 1000 |

The active ingredient is used as a powder wherein at least 90% of the particles are of 63 μm diameter or less.

The above ingredients are mixed directly and pessaries prepared by direct compression of the resulting mixture.

EXAMPLE 7
Topical formulation

|  | Cream |
| --- | --- |
| Active compound | 5.00 g |
| Glycerol | 2.00 g |
| Cetostearyl alcohol | 6.75 g |
| Sodium lauryl sulphate | 0.75 g |
| White soft paraffin | 2.50 g |
| Liquid paraffin | 5.00 g |
| Chlorocresol | 0.10 g |
| Purified water to | 100.00 g |

Dissolve the active compound in a mixture of purified water and glycerol and heat to 70° C. Heat the remaining ingredients at 70° C. Add the two parts together and emulsify. Cool and fill into containers.

What is claimed is:

1. The hemisufate salt of (1S,4R)-cis-4-[2-amino-6-(cyclopropylamino)-9H-purin-9-yl]-2-cyclopentene-1-methanol or a solvate thereof.

2. The compound as claimed in claim 1 in the form of a hydrate.

3. A method for the treatment of an HIV or HBV infection in a human host which comprises administering to said host an effective amount of a compound as claimed in claim 1.

4. A pharmaceutical formulation comprising a compound as claimed in claim 1 and a pharmaeutically acceptable carrier therefor.

5. A pharmaceutical formulation as claimed in claim 4 in the form of a tablet, a capsule, or liquid formulation.

6. A pharmaceutical formulation as claimed in claim 4 adapted for parenteral administration.

7. A dicarboxylate salt of (1S,4R)-cis-4-[2-amino-6-(cyclopropylamino)-9H-purin-9-yl]-2-cyclopentene-1-methanol wherein said dicarboxylate is selected from the group consisting of glutarate, hemisuberate, adipate, fumarate, hemisebacate and pimelate.

8. The glutarate salt of (1S,4R)-cis-4-[2-amino-6-(cyclopropylamino)-9H-purin-9-yl]-2-cyclopentene-1-methanol.

9. A process for the preparation-of the compound claimed in claim 1 which process comprises:

adding sulfuric acid to (1S,4R)-cis-4-[2-amino-6-(cyclopropylamino)-9H-purin-9-yl]-2-cyclopentene-1-methanol in a stoichiometric ratio of approximately 1:2.

10. A process for the preparation of the compound claimed in claim 1 which process comprises:

adding to (1S,4R)-cis-4-2-cyclopentene-1-methanol sulfate (1:1 salt) to (1S,4R)-cis-4-2-cyclopentene-1-methanol in a substantially 1:1 molar ratio in solution.

11. The benzoate or salicylate salt of (1S,4R)-cis-4-[2-amino-6-(cyclopropylamino)-9H-purin-9-yl]-2-cyclopentene- 1 -methanol.

12. A process for the preparation of the compound claimed in claim 1 which process comprises adding (1) sulfuric acid to (2) a salt of (1S,4R)-cis-4-[2-amino-6-(cyclopropylamino)-9H-purin-9-yl]-2-cyclopentene-1-methanol selected from the group consisting of succinate, glutarate, hemisuberate, adipate, fumarate, hemisebacate and pimelate salts and any mixtures thereof, or from the group consisting of benzoate and salicylate salts and any mixtures thereof, wherein said sulfuric acid (1) and said salt (2) are present in the stoichiometric ratio of 2:1 if said salt (2) is a 1:1 salt, and 1:1 if said salt (2) is a 2:1 salt.

13. A pharmaceutical formulation as claimed in claim 4, 5, or 6 additionally comprising one or more therapeutic agents selected from the group consisting of nucleoside HIV reverse transcriptase inhibitors, non-nucleoside HIV reverse transcriptase inhibitors, HIV protease inhibitors, immune modulators selected from the group consisting of interleukin II, erythyropoetin and tucaresol, and α-interferon.

* * * * *

UNITED STATES PATENT AND TRADEMARK OFFICE
CERTIFICATE OF CORRECTION

PATENT NO. : 6,294,540 B1
DATED : September 25, 2001
INVENTOR(S) : Brodie et al.

It is certified that error appears in the above-identified patent and that said Letters Patent is hereby corrected as shown below:

Claim 1,
Delete "hemisufate" and insert therefor -- hemisulfate --.

Signed and Sealed this

Fifth Day of March, 2002

Attest:

Attesting Officer

JAMES E. ROGAN
Director of the United States Patent and Trademark Office